US 8,775,207 B2

(12) United States Patent
Abraham et al.

(10) Patent No.: US 8,775,207 B2
(45) Date of Patent: Jul. 8, 2014

(54) INTEGRATED TREATMENT PLANNING AND SCHEDULING SYSTEM

(75) Inventors: Michele Abraham, Martinez, CA (US); Jean Anderson, Phoenixville, PA (US); Zhanghui Fang, Chester Springs, PA (US); Loretta A. Fitzgerald, Collegeville, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2210 days.

(21) Appl. No.: 11/237,298

(22) Filed: Sep. 28, 2005

(65) Prior Publication Data
US 2006/0173725 A1    Aug. 3, 2006

Related U.S. Application Data

(60) Provisional application No. 60/649,223, filed on Feb. 2, 2005.

(51) Int. Cl.
*G05B 19/418* (2006.01)

(52) U.S. Cl.
USPC ............................ 705/3; 378/65; 705/2; 705/4

(58) Field of Classification Search
CPC ................... A61N 2005/1054; A61N 5/1049; A61N 2005/1061; A61N 5/103; A61N 5/1031
USPC .......... 705/8, 2, 3; 424/184.1; 378/65; 600/2
See application file for complete search history.

(56) References Cited

U.S. PATENT DOCUMENTS

| | | | |
|---|---|---|---|
| 5,113,380 A | | 5/1992 | Levine |
| 5,373,844 A | * | 12/1994 | Smith et al. ................. 600/427 |
| 5,495,284 A | | 2/1996 | Katz |
| 5,530,861 A | | 6/1996 | Diamant et al. |
| 5,558,638 A | | 9/1996 | Evers et al. |
| 5,692,125 A | * | 11/1997 | Schloss et al. .............. 705/7.16 |

(Continued)

FOREIGN PATENT DOCUMENTS

| EP | 090971 A2 | 4/1999 |
|---|---|---|
| EP | 1 065 518 A2 | 1/2001 |

(Continued)

OTHER PUBLICATIONS

Soren Peter Nielsen, et al., "Using Domino Workflow", www.redbooks.ibm.com, May 2000.

(Continued)

*Primary Examiner* — Hiep V Nguyen
*Assistant Examiner* — Teresa Woods
(74) *Attorney, Agent, or Firm* — Joshua B Ryan

(57) ABSTRACT

A system maps components of prescribed treatments to multiple appointments of a patient, tracks patient progress through a course of treatment by recording results of treatment in a clinical information system and replaces multiple manual processes to improve concurrent monitoring of a treatment plan versus actual results. A system schedules multiple appointments for a course of patient treatment. The system uses an input processor for receiving data identifying, a treatment type, a frequency of application of the treatment, a start date of the treatment and a number of applications of the treatment. An appointment processor determines validity of the received data and uses the validated received data to generate data representing a schedule of multiple appointments for receiving the treatment. An interface processor provides data representing the schedule of multiple appointments to a destination system.

16 Claims, 12 Drawing Sheets

(56) References Cited

U.S. PATENT DOCUMENTS

| | | | |
|---|---|---|---|
| 5,711,297 | A * | 1/1998 | Iliff .................... 600/300 |
| 5,721,913 | A | 2/1998 | Ackroff et al. |
| 5,737,728 | A | 4/1998 | Sisley et al. |
| 5,745,901 | A | 4/1998 | Entner et al. |
| 5,758,095 | A | 5/1998 | Albaum et al. |
| 5,764,923 | A | 6/1998 | Tallman et al. |
| 5,772,585 | A | 6/1998 | Lavin et al. |
| 5,786,816 | A | 7/1998 | Macrae et al. |
| 5,790,119 | A | 8/1998 | Sklut et al. |
| 5,799,297 | A | 8/1998 | Goodridge et al. |
| 5,815,566 | A | 9/1998 | Ramot et al. |
| 5,826,239 | A | 10/1998 | Du et al. |
| 5,832,448 | A | 11/1998 | Brown |
| 5,832,455 | A | 11/1998 | Hayashi et al. |
| 5,923,018 | A | 7/1999 | Kameda et al. |
| 5,937,388 | A | 8/1999 | Davis et al. |
| 5,970,466 | A | 10/1999 | Detjen et al. |
| 5,982,863 | A | 11/1999 | Smiley et al. |
| 5,987,422 | A | 11/1999 | Buzsaki |
| 6,024,699 | A * | 2/2000 | Surwit et al. .................... 600/300 |
| 6,037,940 | A | 3/2000 | Schroeder et al. |
| 6,047,259 | A | 4/2000 | Campbell et al. |
| 6,052,669 | A | 4/2000 | Smith et al. |
| 6,052,684 | A | 4/2000 | Du |
| 6,061,657 | A | 5/2000 | Whiting-O'Keefe |
| 6,064,984 | A | 5/2000 | Ferguson et al. |
| 6,067,548 | A | 5/2000 | Cheng |
| 6,078,982 | A | 6/2000 | Du et al. |
| 6,085,184 | A | 7/2000 | Bertrand et al. |
| 6,088,679 | A | 7/2000 | Barkley |
| 6,113,540 | A * | 9/2000 | Iliff .................... 600/300 |
| 6,115,646 | A | 9/2000 | Fiszman et al. |
| 6,151,581 | A | 11/2000 | Kraftson et al. |
| 6,208,345 | B1 | 3/2001 | Sheard et al. |
| 6,208,974 | B1 | 3/2001 | Campbell et al. |
| 6,225,998 | B1 | 5/2001 | Okita et al. |
| 6,277,071 | B1 | 8/2001 | Hennessy et al. |
| 6,278,901 | B1 | 8/2001 | Winner et al. |
| 6,279,009 | B1 | 8/2001 | Smirnov et al. |
| 6,304,886 | B1 | 10/2001 | Bernardo et al. |
| 6,308,160 | B1 | 10/2001 | Rex |
| 6,308,163 | B1 | 10/2001 | Du et al. |
| 6,308,188 | B1 | 10/2001 | Bernardo et al. |
| 6,338,039 | B1 | 1/2002 | Lonski et al. |
| 6,345,260 | B1 * | 2/2002 | Cummings et al. .................... 705/8 |
| 6,347,329 | B1 | 2/2002 | Evans |
| 6,349,238 | B1 | 2/2002 | Gabbita et al. |
| 6,351,770 | B1 | 2/2002 | Li |
| 6,458,080 | B1 | 10/2002 | Brown et al. |
| 6,482,156 | B2 * | 11/2002 | Iliff .................... 600/300 |
| 6,650,930 | B2 * | 11/2003 | Ding .................... 600/436 |
| 6,792,073 | B2 * | 9/2004 | Deasy et al. .................... 378/65 |
| 6,792,074 | B2 * | 9/2004 | Erbel et al. .................... 378/65 |
| 6,824,052 | B2 * | 11/2004 | Walsh .................... 235/380 |
| 7,027,997 | B1 | 4/2006 | Robinson et al. |
| 7,047,535 | B2 | 5/2006 | Lee et al. |
| 7,142,634 | B2 * | 11/2006 | Engler et al. .................... 378/65 |
| 7,240,324 | B2 | 7/2007 | Casati et al. |
| 7,447,644 | B2 | 11/2008 | Brandt et al. |
| 7,899,517 | B2 * | 3/2011 | Kindlein et al. .................... 600/427 |
| 7,907,987 | B2 * | 3/2011 | Dempsey .................... 600/411 |
| 8,244,330 | B2 * | 8/2012 | Meier et al. .................... 600/427 |
| 8,306,185 | B2 * | 11/2012 | Bal et al. .................... 378/65 |
| 8,346,482 | B2 * | 1/2013 | Fernandez .................... 702/19 |
| 8,437,449 | B2 * | 5/2013 | Riley et al. .................... 378/65 |
| 8,440,742 | B2 * | 5/2013 | Cagle .................... 523/160 |
| 2002/0019749 | A1 * | 2/2002 | Becker et al. .................... 705/2 |
| 2002/0046062 | A1 * | 4/2002 | Kameda .................... 705/3 |
| 2002/0059082 | A1 | 5/2002 | Moczygemba |
| 2002/0065701 | A1 | 5/2002 | Kim et al. |
| 2002/0095313 | A1 | 7/2002 | Haq |
| 2002/0120187 | A1 | 8/2002 | Eiffert et al. |
| 2002/0120471 | A1 | 8/2002 | Drazen |
| 2002/0170035 | A1 | 11/2002 | Casati et al. |
| 2003/0036923 | A1 | 2/2003 | Waldon et al. |
| 2003/0050801 | A1 * | 3/2003 | Ries et al. .................... 705/2 |
| 2003/0055679 | A1 | 3/2003 | Soll et al. |
| 2003/0061087 | A1 | 3/2003 | Srimuang |
| 2003/0130870 | A1 | 7/2003 | Tsuchimura |
| 2003/0149714 | A1 | 8/2003 | Casati et al. |
| 2003/0171659 | A1 | 9/2003 | Dean |
| 2003/0208391 | A1 | 11/2003 | Dvorak et al. |
| 2003/0220818 | A1 | 11/2003 | Lemchen |
| 2004/0002873 | A1 | 1/2004 | Sachdeva |
| 2004/0024616 | A1 | 2/2004 | Spector et al. |
| 2004/0039626 | A1 | 2/2004 | Voorhees |
| 2005/0027580 | A1 | 2/2005 | Crici et al. |
| 2005/0075906 | A1 | 4/2005 | Kaindl et al. |
| 2006/0074301 | A1 * | 4/2006 | Meier et al. .................... 600/427 |
| 2006/0173725 | A1 * | 8/2006 | Abraham et al. .................... 705/8 |
| 2006/0274885 | A1 * | 12/2006 | Wang et al. .................... 378/65 |
| 2007/0202119 | A1 * | 8/2007 | Ashdown .................... 424/184.1 |

FOREIGN PATENT DOCUMENTS

| | | | |
|---|---|---|---|
| JP | 10099456 A * | 4/1998 | |
| JP | 2000222507 A * | 8/2000 | |
| JP | 2003175119 A * | 6/2003 | |
| WO | 9924927 A1 | 5/1999 | |
| WO | 00/03344 A1 | 1/2000 | |
| WO | 00/14618 A2 | 3/2000 | |
| WO | 0078374 A1 | 12/2000 | |
| WO | 02099600 A2 | 12/2002 | |

OTHER PUBLICATIONS

Georgakopoulos, et al., An Overview of Workflow Management: From Process Modeling to Workflow Automation Infrastructure:, Distributed and Parallel Databases, Kluwer, NL, vol. 3, No. 2, Apr. 1995, pp. 119-153.

Dewan et al., "Workflow Optimization Through Task Redesign in Business Information Process", IEEE, Jan. 6-9, 1998, pp. 240-252.

Bertino et al., "A Flexible Model Supporting the Specification and Enforcement of Role-based Authorization in Workflow Management Systems", ACM, Nov. 1997, pp. 1-12.

Marazakis et al., "Management of Work Sessions in Dynamic Open Environments", IEEE, Aug. 26-28, 1998, pp. 725-730.

S. Chun, et al., "Dynamic Composition of Workflows for Customized eGovernment Service Delivery", ACM, Mar. 1999, pp. 187-195.

J. Zhao, et al., "Temporal Workflow Management in a Claim Handling System", ACM, Mar. 1999, pp. 187-195.

* cited by examiner

INTEGRATED TREATMENT PLANNING AND SCHEDULING SYSTEM

This is a non-provisional application of provisional application Ser. No. 60/649,223 by M. Abraham et al. filed Feb. 2, 2005.

FIELD OF THE INVENTION

This invention concerns a system for scheduling multiple appointments for one or more courses of patient treatment for one or more medical conditions of a patient as well as associated treatment device and healthcare worker workflow task sequencing.

BACKGROUND OF THE INVENTION

In existing healthcare appointment and scheduling systems, valuable clinician time is expended on clerical work and manual data collation involving transposing information between different systems resulting in error such as misidentification of multiple treatments. Also, planning information, alerts and reminders may be haphazardly and intermittently distributed to other systems or clinicians. Further, in using such existing systems, a clinician spends a portion of each treatment appointment reviewing what occurred during a previous appointment, working out what needs to be done during the present appointment and providing treatment information concerning what needs to be done to a treatment modality device system. In the case of a patient scheduled for radiation therapy, an existing system may be aware of a necessary number of appointments and treatment orders, but these numbers typically are not compatible with the (e.g., one or more) treatment plans involved. Consequently, a clinician needs to work out a connection manually for each appointment. The existing systems also require manual coordination of appointments with treatment plan goals and treatment plan results which occupies a significant amount of clinician time in gathering, collating and analyzing information. A system according to invention principles addresses these deficiencies and associated problems.

SUMMARY OF THE INVENTION

A system maps components of prescribed treatments (body site location, dosage, time) to multiple appointments of a patient and employs a workflow that facilitates efficient patient treatment by communicating specific treatment plan instructions to a treatment modality device system. A system schedules multiple appointments for a course of patient treatment. The system uses an input processor for receiving data identifying, a treatment type, a frequency of application of the treatment, a start date of the treatment and a number of applications of the treatment. An appointment processor determines validity of the received data and uses the validated received data to generate data representing a schedule of multiple appointments for receiving the treatment. An interface processor provides data representing the schedule of multiple appointments to a destination system.

DETAILED DESCRIPTION OF THE INVENTION

Figure 1:
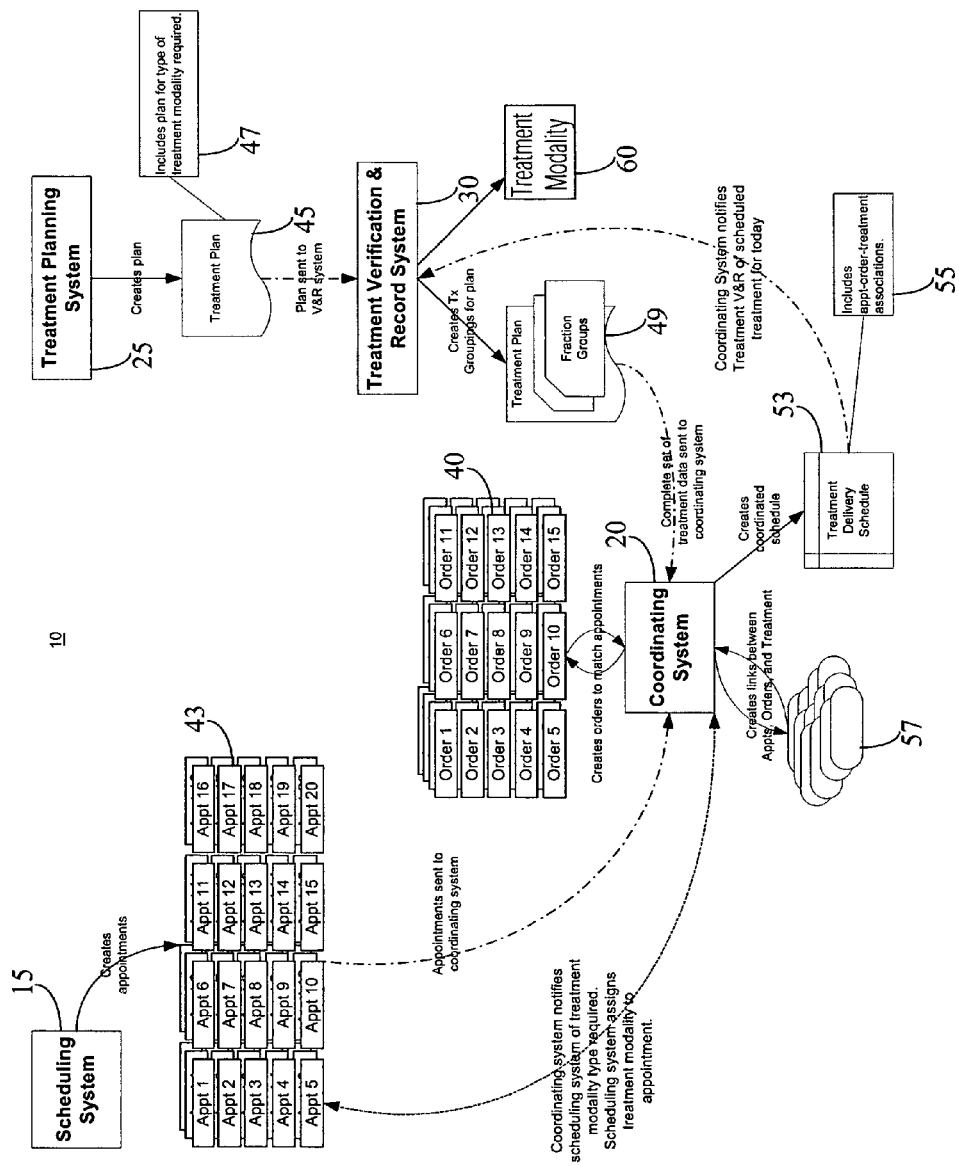
FIG. 1 shows a system for processing information derived from a scheduler and treatment plan to generate an appointment treatment pattern and initiate a task sequence to be performed by a treatment device and a healthcare worker, according to invention principles.

FIG. 1 shows a system for processing information derived from a scheduler and treatment plan to generate an appointment treatment pattern and initiate a task sequence to be performed by a treatment device and a healthcare worker. The inventors have advantageously recognized a need for a system to automatically plan the entire course of a patient treatment, store that plan in a clinical information system and automate generation of associated instructions to a treatment modality device such as a radiation therapy device, sonic device, infusion device or another treatment device. The system provides a Treatment Pattern Generator Workflow that facilitates treatment planning and delivery when treatments are to be provided to a patient over the course of multiple appointments by associating treatment to multiple appointments. The system provides a clinician with a workflow to plan the entire course of treatment, store that plan in the clinical information system, and automate generation of instruction to a treatment modality device. The system provides a clinician with a unified workflow to plan, track, and modify oncology radiation treatments, for example.

An executable application as used herein comprises code or machine readable instruction for implementing predetermined functions including those of an operating system, healthcare information system or other information processing system, for example, in response user command or input. An executable procedure is a segment of code (machine readable instruction), sub-routine, or other distinct section of code or portion of an executable application for performing one or more particular processes and may include performing operations on received input parameters (or in response to received input parameters) and provide resulting output parameters. A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device.

The FIG. 1 system comprises a Clinical Information System (CIS) application that may be used to plan the delivery of a course of oncology radiation treatment, generate an appointment treatment pattern and initiate task sequences to be performed by a radiation treatment device and a healthcare worker, for example. The system generates data representing a pattern of multiple appointments for a patient to receive one or more different treatments and re-configures appointments in response to a missed appointment, in order to maximize efficient use of treatment devices, healthcare personnel and to minimize patient inconvenience. The system advantageously adaptively derives a pattern of multiple appointments to facilitate delivery of multiple different compatible prescribed treatments during an individual single appointment. For this purpose, in the radiation treatment delivery example, the system derives a pattern of multiple appointments by determining compatibility of different treatments based on factors including body site location of radiation treatment, dosage and time of treatment. The system derives associated task sequences (workflows) employed by a radiation treatment device and healthcare workers that facilitate efficient patient treatment. The system also sends data comprising instructions to treatment modality devices (including a radiation treatment device) implementing a specific treatment plan in accordance with a derived appointment pattern. The system further tracks patient progress through a course of treatment by recording results of treatment and advantageously automates appointment generation, associated workflow generation and concurrent monitoring of a treatment plan and corresponding treatment outcomes.

System 10 of FIG. 1 is incorporated in a clinical information system (CIS) and includes a coordinator 20 that is linked to scheduling system 115 and treatment verification and record system 30. In response to user command and data entry indicating a prescribed treatment of a particular patient medical condition, treatment planning system 25 generates a treatment plan 45 including an associated plan 47 for a particular type of treatment modality device to be used in administering the planned treatments. The treatment plan 45 is provided to treatment verification and record system 30 which groups individual compatible treatments into one or more types of groupings to create treatment data 49 that is communicated to coordinator 20. Data 49 also includes information indicating one or more treatment modality devices used to provide the grouped treatments. In response to received data 49, coordinator 20 communicates data indicating treatment modality device type (and/or a particular device) to be used for providing particular patient treatments to system 15.

In response to user command and data entry indicating a prescribed treatment of a particular patient medical condition and data from coordinator 20, scheduling system 15 creates appointments to administer the treatments to a patient. For this purpose, system 15 associates a particular treatment modality device type (and/or a particular device) to one or more appointments 43. Scheduling system 15 provides data identifying appointments 43 to coordinator 20. In response, coordinator 20 creates orders for treatment 40 to match appointments 43. Coordinator 20 using at least one repository, associates appointments 43, orders for treatment 40 and treatment data 49 and creates a coordinated treatment delivery schedule comprising treatment appointment calendar 53 including data 55 indicating association of appointments 43 with orders for treatment 40 and with treatment data 49. The treatment appointment calendar 53 is also communicated to treatment verification and record system 30. The data is used to schedule task sequences of treatment delivery modality device 60 and healthcare workers. Coordinator 20 advantageously associates treatments to appointments, not just to calendar dates and ensures an individual treatment remains associated with its corresponding appointment even if a patient misses, postpones or reschedules the corresponding appointment. Coordinator 20 also automatically provides data indicating task sequences (workflows) that enable a user to choose a treatment plan or portion of a plan and to select appointment treatment pattern 40.

Figure 6:
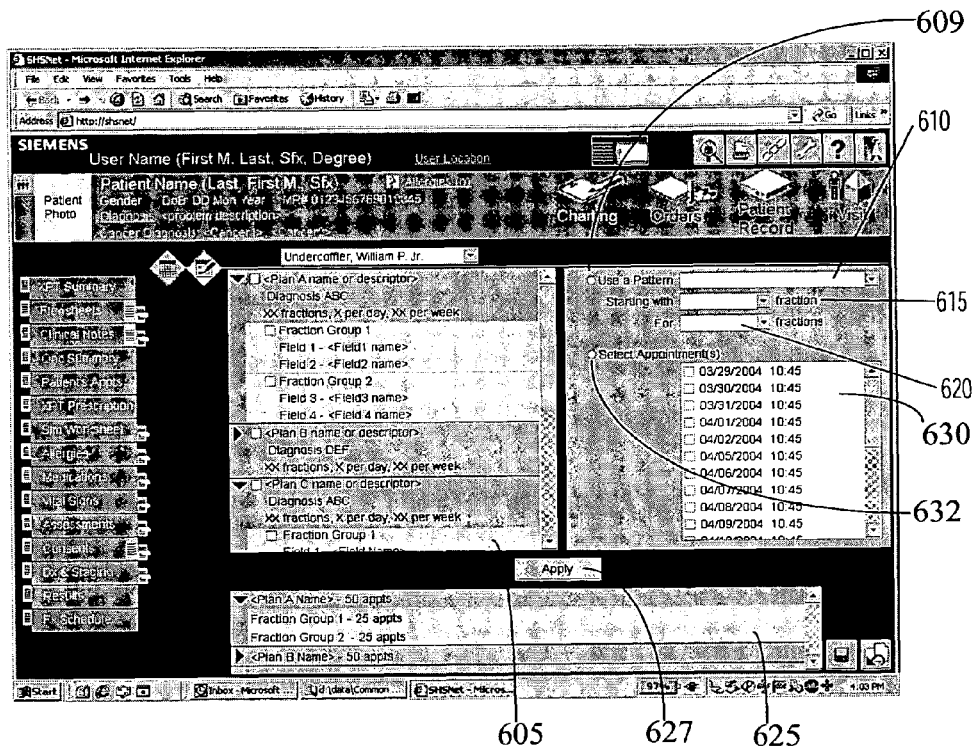
FIG. 6 shows an appointment generation user interface image, according to invention principles.

A workflow created by coordinator 20 enables a user of system 10 to select a pattern (daily, every other day, every third day, etc.) and indicate when it should start and how often it should repeat. A user does not have to select each day or appointment individually. FIG. 6 shows an appointment generation user interface image enabling a user to enter treatment plan data via image window 625 and to select previously entered treatment plan data via image window 605 as well as to apply selected treatment plan data by selection of button 627. Treatment plan data is presented in user selectable collapsible and expandable blinds within image window 605. A user is able to initiate generation of an appointment pattern by selection of an icon 609 and a pattern type (e.g., every other day, every two days, three days, once a week, or month etc.) using option list 610. A user selects a treatment or treatment group to start a selected pattern using option list 615 and selects another treatment or treatment group to use in the selected pattern using option list 620. A user is also able to select one or more particular appointments (created by scheduling system 15) to be used in the desired pattern via box 630 and associated user selectable icon 632.

Thereby, if one portion of a first course of treatment comprising 25 individual treatments, is to be administered to a patient on alternate occasions over the course of 50 appointments of a different second course of treatment, a clinician does not have to manually select the 25 appointments. System 10 advantageously automatically generates appropriate links associating individual treatments to corresponding appointments in response to user entered data indicating a particular appointment treatment pattern.

System 10 advantageously integrates treatment modality device 60 with a clinical information system and provides information from coordinator 20 to treatment modality device 60 indicating appointments and associated treatments and also associated treatment modality device operational instruction. This allows a clinician to spend more time with a patient by reducing the time needed to be spent on entering treatment directions into a treatment modality system.

Figure 3:
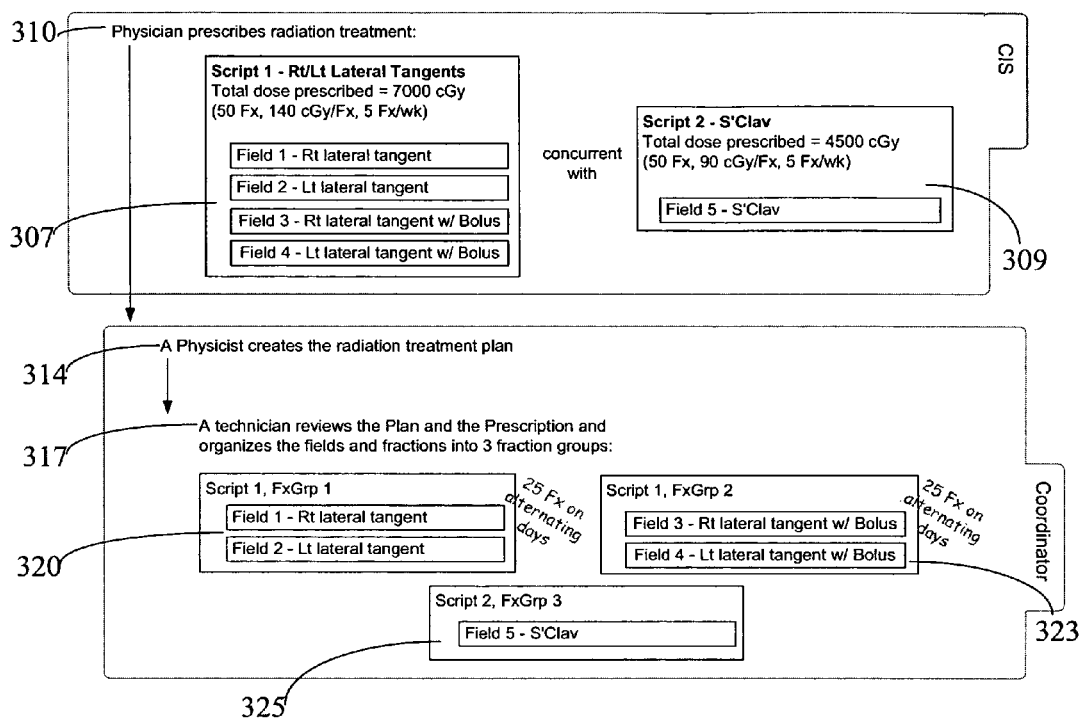
FIGS. 3, 4 and 5 illustrate appointment and treatment plan generation using the system of FIG. 1, according to invention principles.
Figure 4:
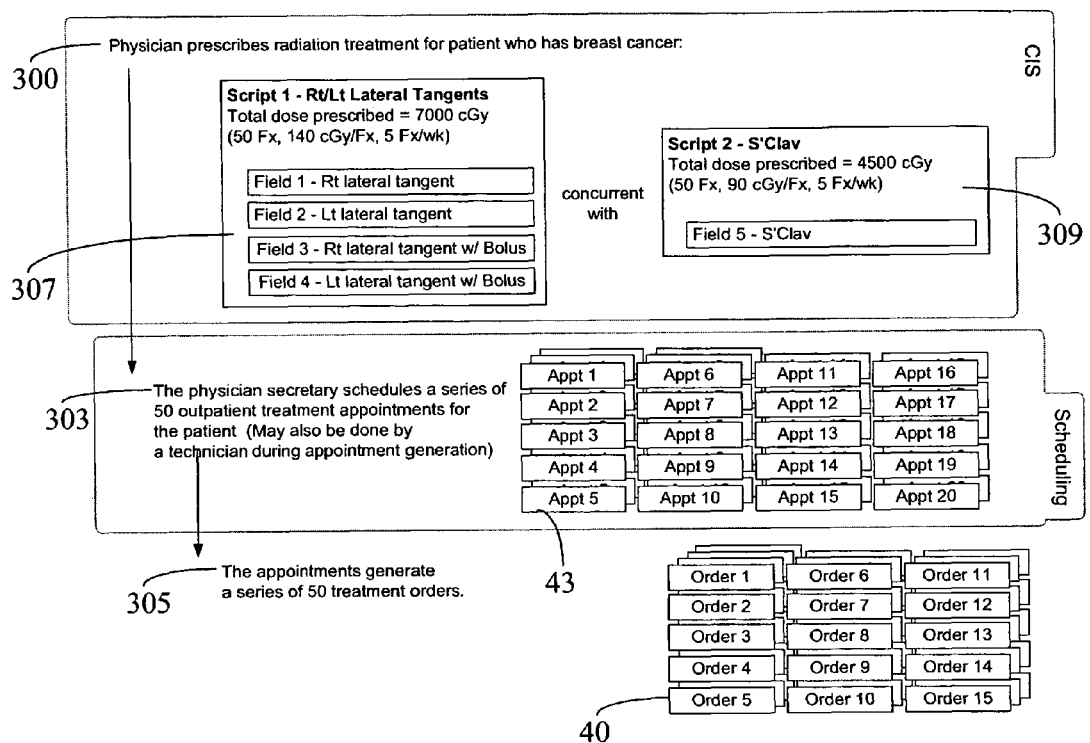
Figure 5:
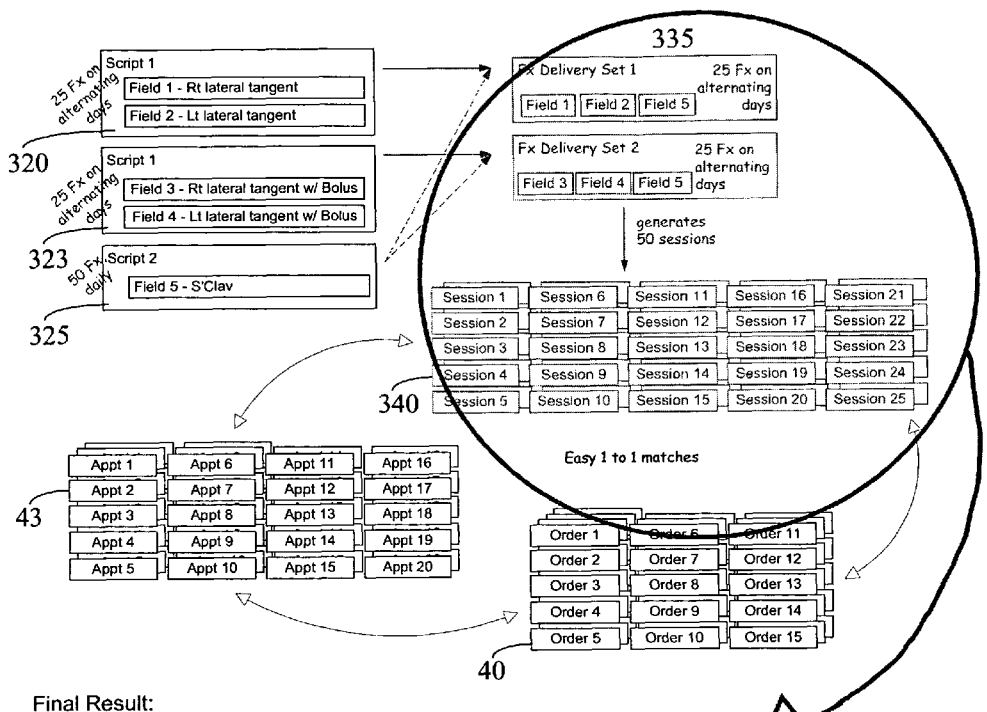

FIGS. 3, 4 and 5 illustrate appointment and treatment plan generation using the system of FIG. 1. In step 310 of FIG. 3 a physician prescribes radiation treatment for a patient that has breast cancer. The physician employs treatment planning system 25 to prescribe radiation therapy for two different anatomical sites to be applied concurrently. A first anatomical site is to be treated with a first treatment 307 delivering radiation from two different sides but in order to achieve the necessary amount of radiation, a bolus (a fixed radiation source) modifier is used every other day of treatment. The second anatomical site (S'Clav) receives a second different treatment 309 delivering a standard daily dose of treatment. The physician indicates that the therapy is to be administered over the course of 50 appointments.

In response to physician data entry, treatment planning system 25 generates a treatment plan 45 including an associated plan 47 for the radiation treatment modality device to be used in administering the planned treatments. The treatment plan 45 is provided to treatment verification and record system 30, in response to user command in step 314. In step 317 a technician reviews the created treatment plan 45 and prescription and directs unit 30 in step 317 to create treatment data 49 representing grouped treatments 320 (FxGrp 1) and 323 (FxGrp2) to be delivered on 25 alternating days for a total of 50 days as well as grouped treatment 325 (FxGrp 3) to be delivered on each day of the total of 50 days. Unit 30 communicates treatment data 49 to coordinator 20. In addition coordinator 20 provides data 49 to scheduling system 15. Data 49 also includes information identifying a treatment modality device and bolus used to provide the grouped treatments. In another embodiment unit 30 automatically creates treatment data 49.

In response to user command and data entry in step 300 of FIG. 4 indicating the prescribed treatment, a user in step 303 employs scheduling system 15 to create a series of 50 outpatient treatment appointments to receive treatments 307 and 309. System 15 provides data identifying the appointments 43 for treatments 307 and 309 (grouped into three groups 320, 323 and 325) to coordinator 20 in step 305. In response, coordinator 20 creates orders for treatment 40 to match appointments 43 as previously explained in connection with FIG. 1. In another embodiment, system 15 automatically creates appointments 43 in response to data entry in step 300 indicating the prescribed treatment or in response to received treatment data 49 and without user direction.

FIG. 5 illustrates generation by units 30, 15 and 20 of data representing treatment appointments 43, associated orders 40 and a corresponding treatment appointment calendar 53. Unit 30 advantageously automatically generates treatment data 49, in response to user entered treatment appointment pattern selection information. Treatment data 49 represents grouped treatments 320 and 323 to be administered to a patient on 25 alternating days for a total of 50 days as swell as grouped treatment 325 to be delivered on each day of the total of 50 days, for example. Unit 30 communicates treatment data 49 to coordinator 20 which provides data 49 to scheduling system 15.

Scheduling system 15 automatically creates a series of 50 outpatient treatment appointments 43 to receive grouped treatments 335 (incorporating groups 320, 323 and 325) in response to user entered data indicating the prescribed treatment or in response to received treatment data 49 and without user direction. In response to receiving appointment data 43, coordinator 20 creates orders for treatment 40 to match appointments 43 as well as data representing treatments to occur at the appointment sessions 340. Coordinator 20 further provides treatment appointment calendar 53 based on appointment data 43, treatment order data 40 and appointment session data 340. Treatment appointment calendar 53 indicates for individual appointment sessions on corresponding individual calendar dates, an appointment number (e.g., 1-50), a treatment order number (e.g., 1-50) and the treatments to be administered identified by treatment group identifier (FxGrp 1, FxGrp 2 or FxGrp 3 corresponding to treatment groups 320, 323 and 325 respectively).

Figure 7:
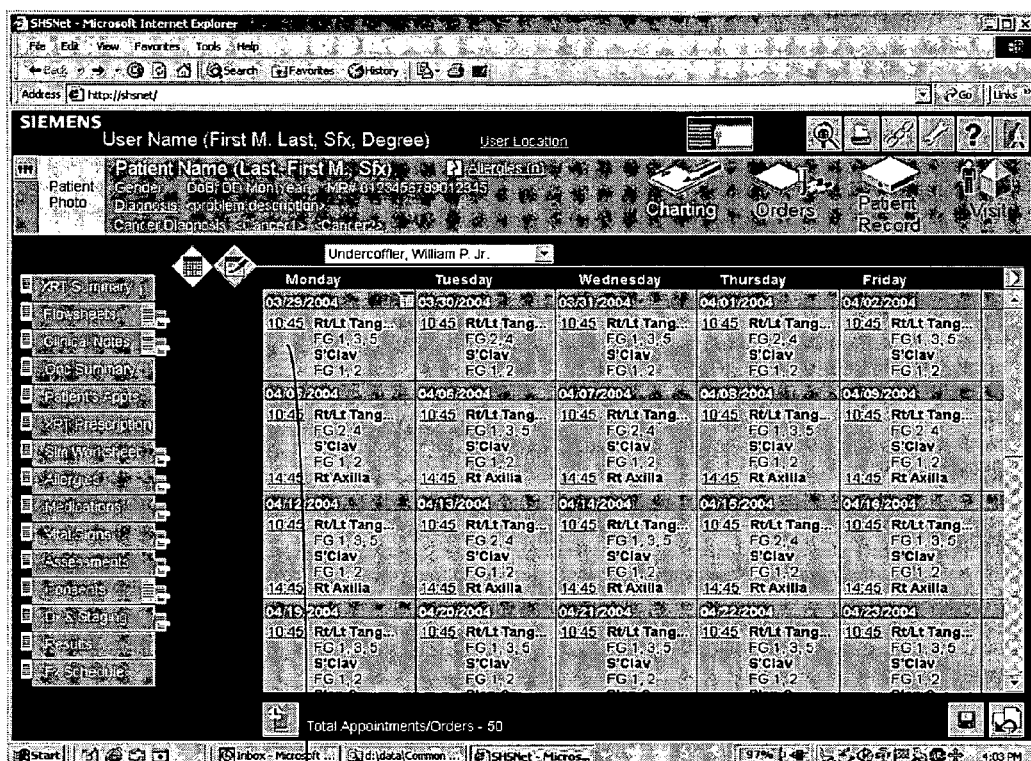
FIG. 7 shows an appointment calendar user interface image, according to invention principles.
Figure 8:
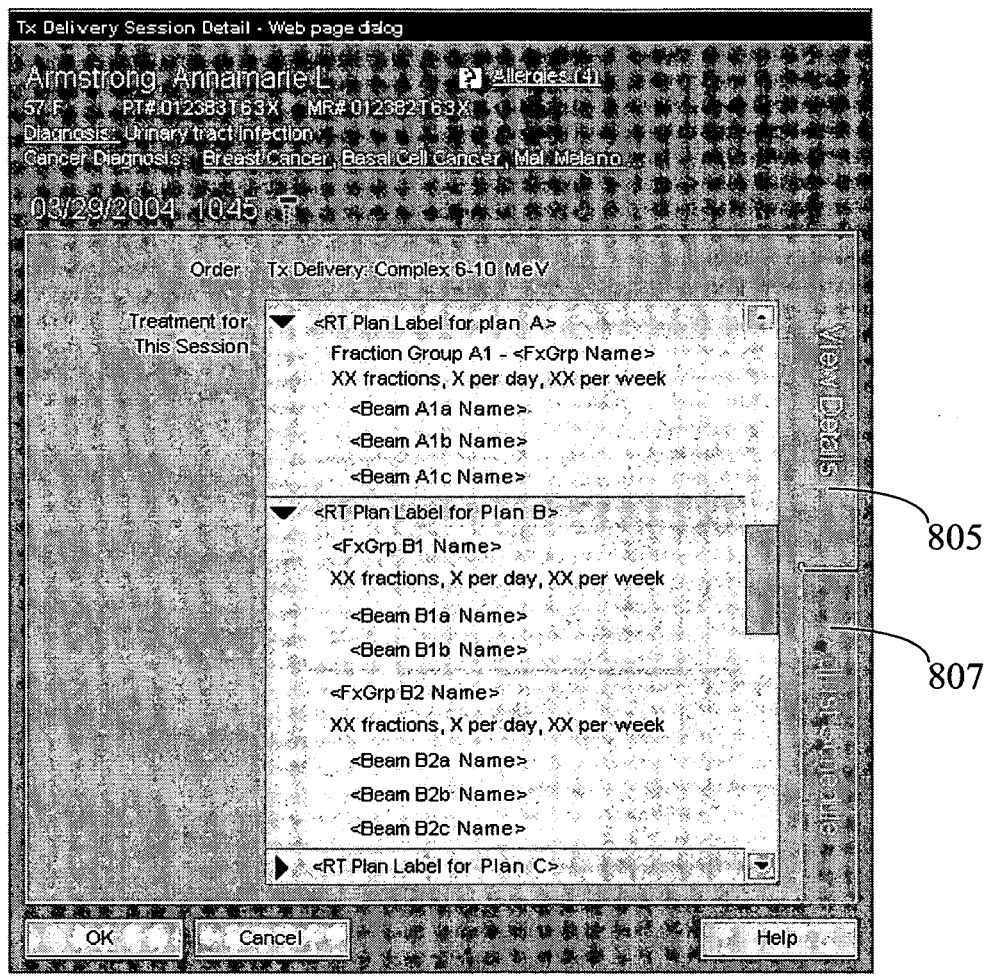
FIGS. 8 and 9 show user interface image windows showing treatment information and enabling treatment modification, according to invention principles.
Figure 9:
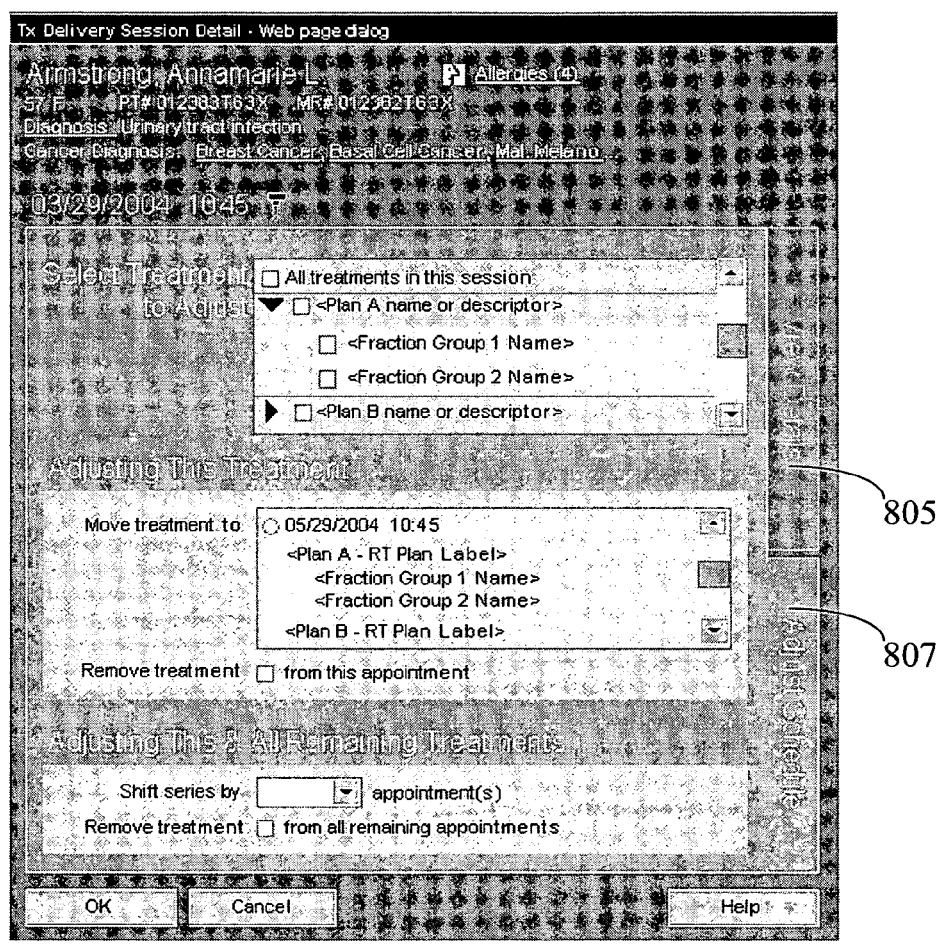

FIG. 7 shows another format of appointment calendar 53 in a user interface image Internet browser window provided by system 10. This treatment appointment calendar format indicates for individual appointment sessions on corresponding individual calendar dates, the times of treatment appointments, an identifier of anatomical features to be treated (e.g., Rt/Lt Tang, S'Clav) and the treatments to be administered identified by treatment group identifier (e.g., FG 1, 2, 3, 5). FIGS. 8 and 9 show user interface image windows provided by system 10 showing treatment information and enabling treatment modification. The FIG. 8 image window corresponding to user selectable image tab 805, is displayed in response to user selection of appointment 705 in the treatment appointment calendar of FIG. 7 and enables a user to see detailed treatment information concerning appointment 705 (of Mar. 29, 2004). The user is also able to adjust the scheduled treatment using the FIG. 9 image window displayed in response to user selection of image tab 807.

Figure 2:
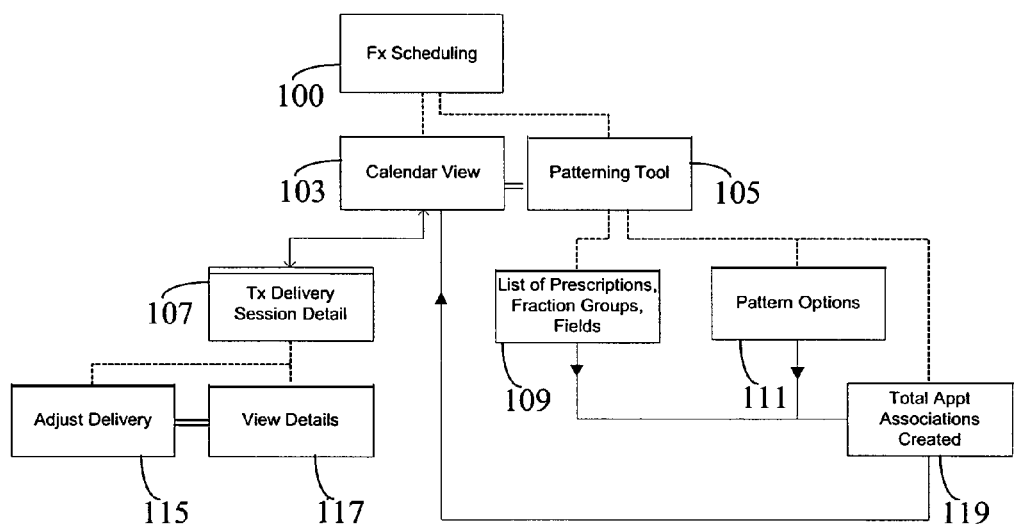
FIG. 2 shows user interface interaction and workflow involved in generating an appointment treatment pattern and initiating a task sequence, according to invention principles.

FIG. 2 shows the user interface interaction and workflow involved in generating an appointment treatment pattern and initiating a task sequence. In response to user creation of a treatment plan, coordinator 20 automatically provides data indicating a task sequence comprising a treatment administration workflow. In step 100 of the workflow, a clinician employs a user interface image provided by treatment planning system 25 to select a patient to be treated from an online appointment list and to initiate a treatment task. An appointment pattern generator provided by system 10 provides treatment appointment calendar 53 based on appointment data 43 as well as treatment order data 40 and appointment session data 340 in step 105. Treatment verification and record system 30 in step 109 provides data indicating treatments including a list of prescriptions for a patient as well as identifying individual treatment groups (such as treatment groups 320, 323 and 325 of FIGS. 3 and 5) to coordinator 20. In step 111 system 10 provides a user interface image enabling a user to enter data and initiate generation of an appointment pattern configured in response to user selected pattern generation options as previously described in connection with the display image of FIG. 6. Coordinator 20 creates associations in step 119 that link orders for treatment to matching appointments as well as to treatments to occur at appointment sessions and a treatment appointment calendar (e.g., calendar 53 of FIG. 5).

A clinician in step 103 selects a particular patient appointment and accesses information indicating treatment planned for the selected appointment via treatment appointment calendar 53 as previously described in connection with FIGS. 5 and 7. Coordinator 20 in step 107 communicates information concerning the planned treatment to treatment modality system 60 via treatment verification and record system 30. Treatment modality system 60 displays patient and planned treatment related information to a clinician and enables a clinician to adjust planned treatment or to initiate treatment via user interface images similar to those of FIGS. 7-9 in steps 115 and 117.

Figure 10:
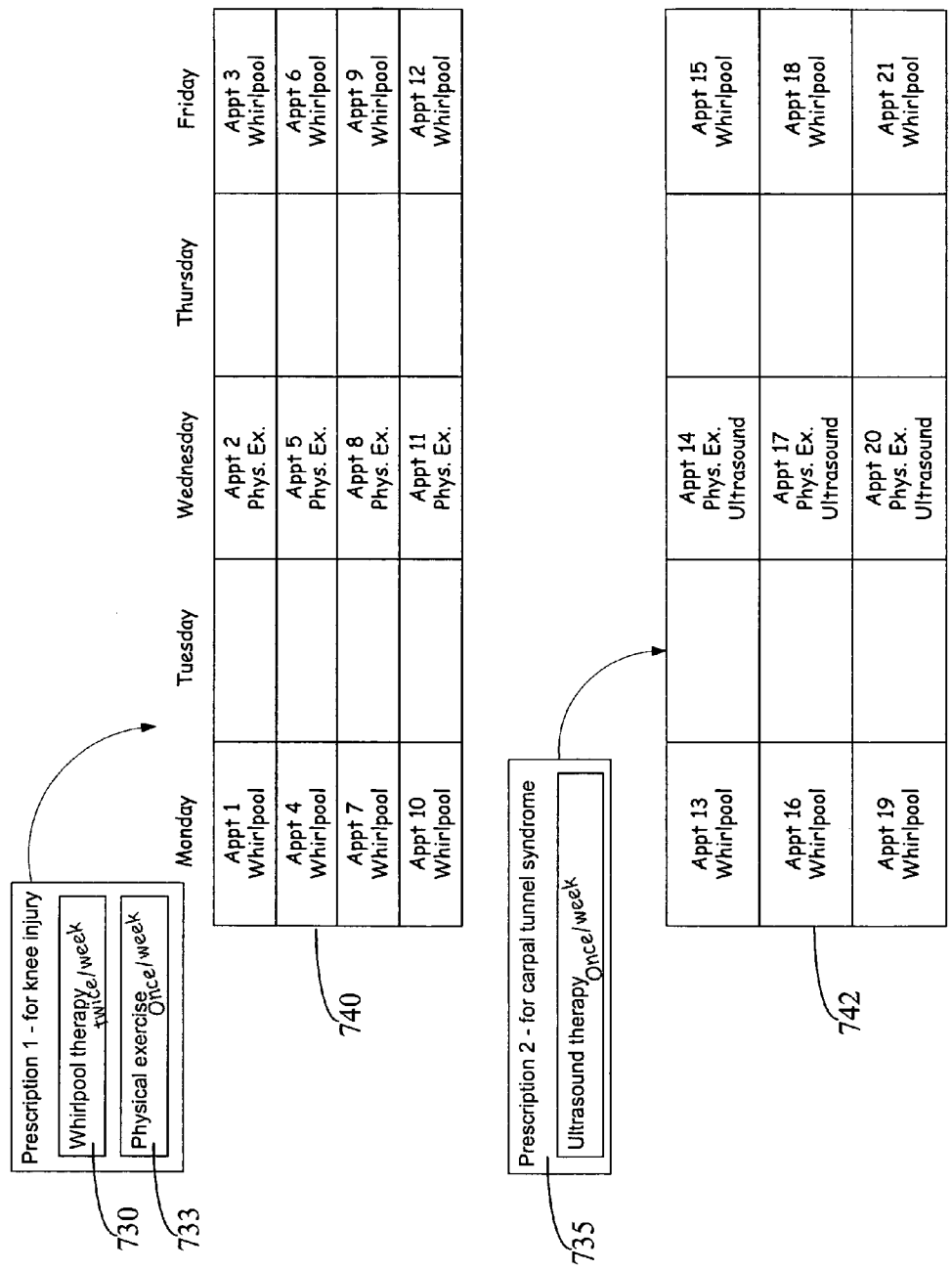
FIG. 10 illustrates appointment generation for intermingled different treatments, according to invention principles.

FIG. 10 illustrates system 10 adaptively generate treatment appointments for intermingled different treatments. Coordinator 20 automatically creates associations that link orders and appointments for different treatments 730 and 733 comprising whirlpool therapy to occur twice per week and physical exercise to occur once per week over a period of ten weeks to comprise a total of thirty appointment sessions to address a patient knee injury. After four weeks following initiation of the ten week treatment cycle, a further twelve sessions of ultrasound therapy treatment 735 comprising one session per week is prescribed for the patient to address a carpal tunnel syndrome condition. In response to receiving data indicating that additional treatment 735 is prescribed for the patient, coordinator 20 adaptively automatically generates associations that link orders and appointments for different treatments 730, 733 and 735. Coordinator 20 automatically creates and links orders and matching appointments (derived from system 15) as well as treatments to occur at appointment sessions and a treatment appointment calendar (e.g., calendar 53 of FIG. 5). A resultant appointment calendar 742 incorporates appointments for treatments 730, 733 and 735 following four weeks of appointments for treatments 730 and 733 indicated in prior treatment calendar 740.

Figure 11:
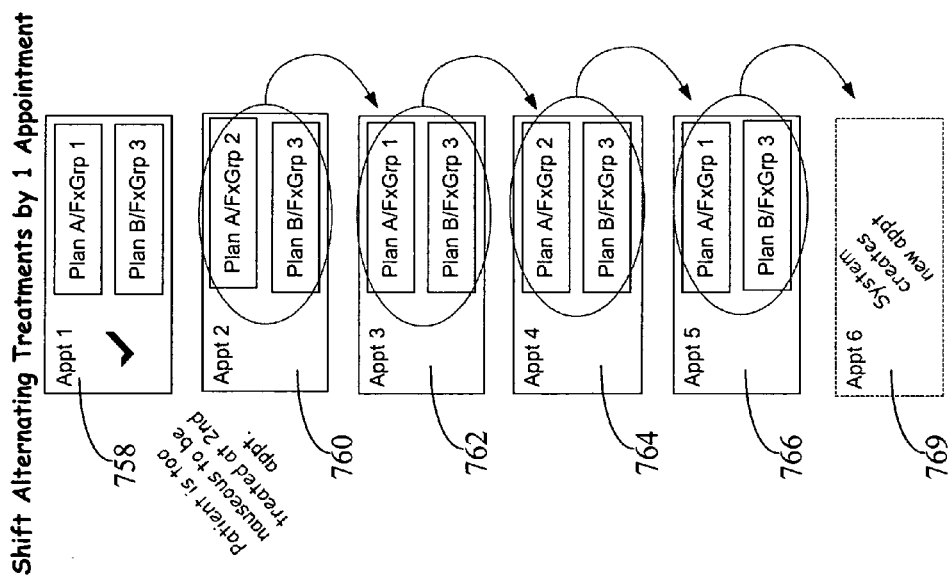

FIG. 11 illustrates system 10 adaptively generate treatment appointments accommodating a missed appointment. A patient is scheduled for five appointments 758-766 in order to receive alternating treatments FxGrp1 and FxGrp2 together with treatment FxGrp3. After first appointment 758, a patient is unable to receive a scheduled second appointment 760 due to illness. System 10 automatically shifts appointments by a single appointment delay to accommodate missed appointment 760. Thereby appointment 2 (760) is shifted to appointment 3(762), appointment 3 (762) is shifted to appointment 4 (764), appointment 4 (764) is shifted to appointment 5 (766) and appointment 5 (766) is shifted to become a newly created appointment 6 (769). Coordinator 20 creates associations that link orders and matching appointments (derived from system 15) as well as treatments to occur at appointment sessions and a treatment appointment calendar for the new series of treatment appointments 760-769.

Figure 12:
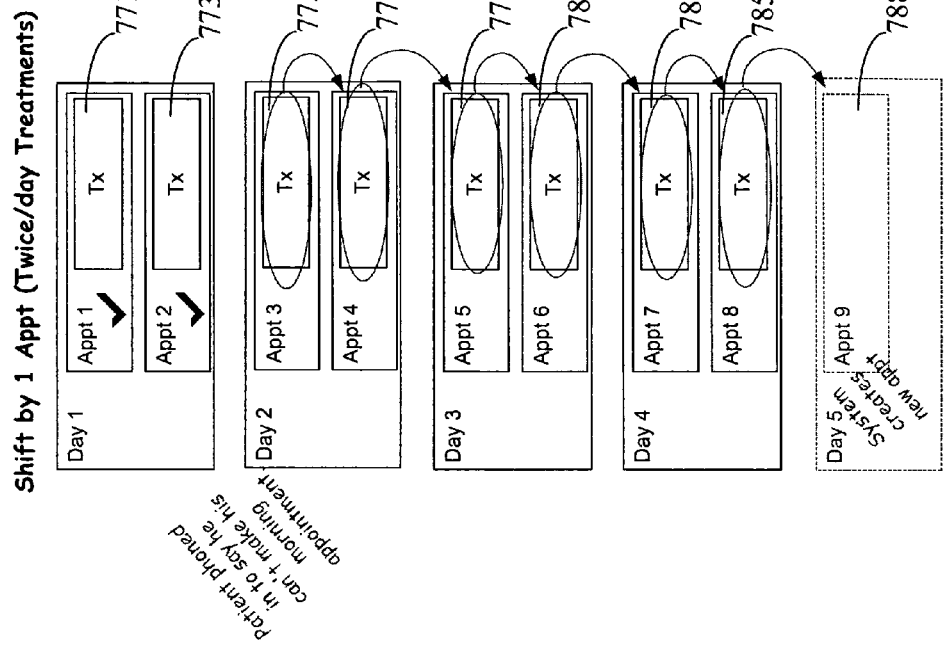
FIGS. 11 and 12 illustrate appointment generation accommodating a missed appointment, according to invention principles.

FIG. 12 like FIG. 11, illustrates system 10 adaptively generate treatment appointments accommodating a missed appointment. A patient is scheduled for eight appointments 771-785 over four days to receive a treatment twice per day. After the first two appointments 771 and 773, a patient misses third appointment 775. System 10 automatically shifts appointments by a single appointment delay to accommodate missed appointment 775. Thereby appointment 3 (775) is shifted to appointment 4 (777), appointment 4 (777) is shifted to appointment 5 (779), appointment 5 (779) is shifted to appointment 6 (780), appointment 6 (780) is shifted to appointment 7 (783), appointment 7 (783) is shifted to appointment 8 (785) and appointment 8 (785) is shifted to become a newly created appointment 9 (788). Coordinator 20 automatically creates associations that link orders and appointments for the new series of treatment appointments 777-788. Coordinator 20 creates and links orders and matching appointments (derived from system 15) as well as treatments to occur at appointment sessions and a treatment appointment calendar for the new series of treatment appointments 777-788.

Figure 13:
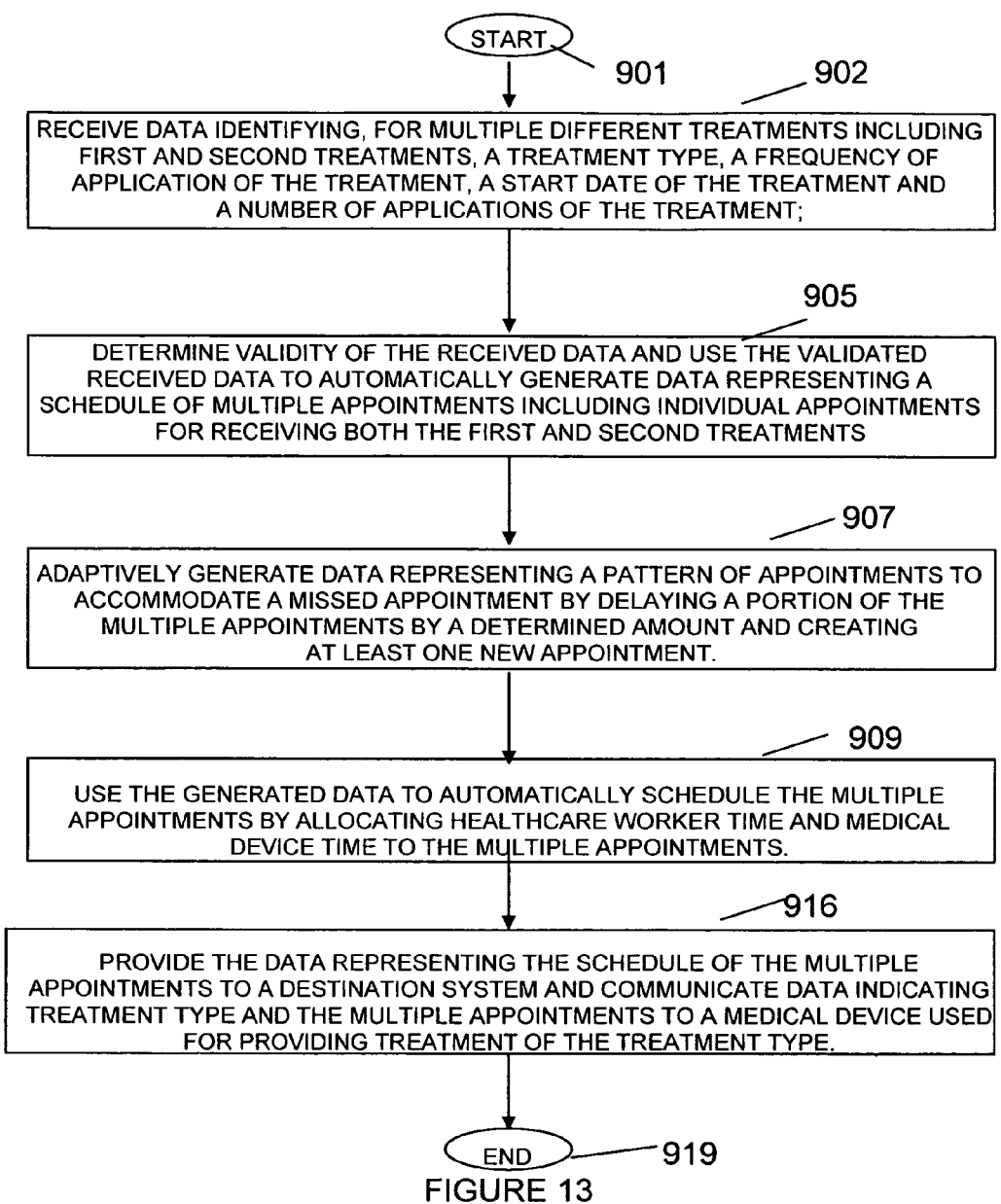
FIG. 13 shows a flowchart of a process for generating an appointment treatment pattern and initiating a task sequence to be performed by a treatment device and a healthcare worker, according to invention principles.

FIG. 13 shows a flowchart of a process for generating an appointment treatment pattern and initiating a task sequence to be performed by a treatment device and a healthcare worker. In step 902 following the start at step 901, system 10 receives data identifying, for multiple different treatments including first and second treatments, a treatment type, a frequency of application of a treatment, a start date of a treatment and a number of applications of a treatment. In one example of operation, the treatment type information identifies first and second anatomical parts of a patient and the first and second treatments comprise first and second radiation doses to be applied to the first and second anatomical parts respectively, for example. In another example of operation, the treatment type information identifies an anatomical part of a patient and the first treatment comprises a radiation dose to be applied to the anatomical part and the second treatment comprises a non-radiation therapy. The frequency of application of a treatment comprises at least one of, (a) daily, (b) weekly, (c) on alternate days, (d) on every third day, on every fourth day and so on, (e) hourly, (f) on alternate hours and (g) on every third hour, on every fourth hour and so on. The received data also identifies an end date of the treatment and includes data identifying a medical device for use in administering the multiple different treatments.

In step 905 system 10 automatically determines validity of the received data and uses the validated received data to generate data representing a schedule of multiple appointments including individual appointments for receiving both the first and second treatments. The schedule of multiple appointments comprises a pattern of individual appointments for receiving both the first and second treatments and minimizing a number of patient visits to a healthcare facility. System 10 determines validity of the received data by determining the number of applications of treatment is consistent with at least one of, (a) the treatment type and (b) the frequency of application of the treatment. System 10 also determines validity of the received data by determining the medical device for use in administering the multiple different treatments is compatible with the treatment type. System 10 in step 907 adaptively generates data representing a pattern of appointments to accommodate a missed appointment by delaying a portion of the multiple appointments by a determined amount and creating at least one new appointment. System 10 determines the amount to be a delay comprising a shift to a next subsequent appointment or a shift to a subsequent appointment following the next subsequent appointment.

In step 909 system 10 uses the generated data to automatically schedule the multiple appointments by allocating healthcare worker time and medical device time to the multiple appointments. In step 916 system 10 provides the data representing the schedule of the multiple appointments to a destination system and communicates data indicating treatment type and the multiple appointments to a medical device used for providing treatment of the treatment type. The data communicated to the medical device includes medical device settings used for configuring the medical device to provide treatment for an individual appointment. The process of FIG. 13 terminates at step 919.

System 10 advantageously integrates scheduling system 15 with treatment planning system 25 and treatment modality 60 and includes coordinator 20 enabling the central coordination of treatment appointments, treatment orders, and plans. System 10 also includes a pattern generator enabling a user to select a treatment appointment pattern, indicate the pattern starting point and a number of repetitions and automatically generate appropriate links between a prescribed treatment and scheduled appointments.

The system, user interface image menus and processes presented in FIGS. 1-13 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system is usable for radiation and other types of therapy where repetitive treatment (e.g., radiation or chemotherapy) is provided on a recurring basis over an extended period of time, and is especially useful for therapies where treatment is administered under more than one prescription or treatment plan at a time. For example, system 10 plans and tracks therapies for a patient in physical therapy for a knee injury—requiring treatment 3×/week—receiving whirlpool treatments on an alternating schedule with treadmill and other supervised physical exercise. If the patient also develops a secondary condition, such as carpal tunnel syndrome, system 10 allows the therapist to add the treatment for that condition (1×/week—receiving ultra sound treatment), updating the schedule so that the physical therapist can readily see which therapies are to be administered at each session.

System 10 advantageously automatically recovers from missed appointments (e.g., by restarting appointments or altering therapy) and is usable for intermingled different therapies. Further, system 10 advantageously communicates messages to treatment modality devices including device settings and safety check data and performs appointment safety cross checks. Further, any of the functions provided by the system of FIG. 1 and processes of FIGS. 2-5 and 10-13 may be implemented in hardware, software or a combination of both.

What is claimed is:

1. A system for scheduling multiple appointments for a course of patient treatment, comprising:

a treatment planning system configured to receive a plurality of prescribed treatments, each prescribed treatment comprising an indication of treatment body site location, treatment type, frequency of treatment application, treatment start date, and number of treatment applications;

a treatment verification system configured to:
automatically identify one or more compatible treatment sets in the plurality of prescribed treatments, each compatible treatment set comprising prescribed treatments capable of being performed during a single appointment, create a treatment plan comprising one or more of the one or more compatible treatment sets, and
create an associated plan for one or more modality devices to be used in administering the treatment plan;

an appointment processor configured to automatically generate data representing a schedule of appointments over a plurality of days for receiving prescribed treatments included in the treatment plan;

a coordinating system configured to:
automatically generate data representing treatment orders for each respective appointment in the schedule of appointments,
automatically generate a plurality of instruction sets for execution by the one or more modality devices, and
associating each of the plurality of instruction sets with a distinct appointment in the schedule of appointments; and a treatment modality system operably coupled to the one or more modality devices and configured to:
receive a user selection of a current appointment included in the schedule of appointments,
select an associated instruction set from the plurality of instruction sets based on the user selection of the current appointment, and
initiate execution of the set by the one or more modality devices.

2. A system according to claim 1, wherein the appointment processor is further configured to:
determine whether each prescribed treatment included in the treatment plan is valid by determining whether its respective number of treatment applications is consistent with at least one of (a) its respective treatment type and (b) its respective frequency of treatment application.

3. A system according to claim 1, wherein the appointment processor is further configured to:
adaptively generate data representing an adjusted schedule of appointments to accommodate a missed appointment by delaying a portion of the appointments in the schedule of appointments by a determined amount and creating at least one new appointment.

4. A system for scheduling multiple appointments for a course of patient treatment, comprising:

a treatment planning system configured to receive a plurality of prescribed treatments, each prescribed treatment comprising an indication of treatment body site location, treatment type, frequency of treatment application, treatment start date, and number of treatment applications;

a treatment verification system configured to:
automatically identify one or more compatible treatment sets in the plurality of prescribed treatments, each compatible treatment set comprising prescribed treatments capable of being performed during a single appointment, and
create a treatment plan comprising one or more of the compatible treatment sets, and
create an associated plan for one or more modality devices to be used in administering the treatment plan, the associated plan comprising a plurality of instruction sets executable by the one or more modality devices;

an appointment processor configured to:
automatically generate data representing a schedule comprising a pattern of a plurality of appointments over a plurality of days including individual appointments for receiving prescribed treatments included in the treatment plan,
associate each of the plurality of instruction sets in the associated plan with a distinct appointment in the plurality of appointments, and
adaptively generate data representing an adjusted pattern of appointments to accommodate a missed appointment by delaying a portion of the plurality of appointments by a determined amount and creating at least one new appointment; and a treatment modality system operably coupled to the one or more modality devices and configured to:
identify a current appointment from the plurality of appointments;
select an associated instruction set from the plurality of instruction sets in response to the identification of the current appointment, and
initiate execution of the associated instruction set by the one or more modality devices.

5. A system according to claim 4, wherein the frequency of treatment application for each of the plurality of prescribed treatments comprises at least one of, (a) daily, (b) weekly, (c) on alternate days, (d) on every third day.

6. A system according to claim 4, the frequency of treatment application for each of the plurality of prescribed treatments comprises at least one of, (a) hourly, (b) on alternate hours, (d) on every third hour and (e) on every fourth hour and so on.

7. A system according to claim 4, wherein each prescribed treatment further comprises a treatment end date.

8. A system according to claim 4, wherein the appointment processor is further configured to:
determine validity of the prescribed treatments by determining whether the number of treatment applications associated with each prescribed treatment is consistent with at least one of (a) its treatment type and (b) its frequency of treatment application.

9. A system according to claim 4, wherein
the appointment processor is further configured to determine validity of the first prescribed treatment by determining whether the one or more modality devices are compatible with a corresponding treatment type associated with the first prescribed treatment.

10. A system for scheduling multiple appointments for a course of patient treatment, comprising:
an integrated treatment planning system communicating with a clinical information system and configured to:
receive treatment data identifying, for a plurality of prescribed treatments including first and second prescribed treatments to be applied to first and second different body sites of a single patient,
a treatment type,
a frequency of application of a treatment,
a start date of the treatment, and
a number of applications of the treatment;
a treatment verification system configured to:
automatically identify one or more compatible treatment sets in the plurality of prescribed treatments, each compatible treatment set comprising prescribed treatments capable of being performed during a single appointment, and
create a treatment plan comprising one or more of the compatible treatment sets, and
create an associated plan for one or more medical devices to be used in administering the treatment plan;
an appointment processor configured to automatically:
determine validity of the prescribed treatments in the compatible treatment sets, use the compatible treatment sets to generate data representing a schedule comprising a pattern of a plurality of appointments over a plurality of days including individual appointments for receiving each of the prescribed treatments in the compatible treatment sets, and
adaptively generate data representing the pattern of appointments to accommodate a missed appointment by delaying a portion of the plurality of appointments by a determined amount and creating at least one new appointment; and
a coordinating system configured to:
automatically generate data representing treatment orders for each appointment in the schedule,
automatically generate a plurality of instruction sets associated with the treatment orders for execution by the one or more medical devices, and
associate each of the plurality of instruction sets in the associated plan with a distinct appointment in the schedule;
a task processor configured to automatically schedule the plurality of appointments by allocating healthcare worker time and medical device time to the plurality of appointments; and
a treatment modality system operably coupled to the one or more medical devices and configured to:
identify a current appointment from the schedule;
select an associated instruction set from the plurality of instruction sets in response to the identification of the current appointment, and
initiate execution of the associated instruction set by the one or more medical devices.

11. A system according to claim 10, wherein the schedule comprises a pattern of individual appointments for receiving both the first and second prescribed treatments.

12. A system according to claim 10, further comprising:
a communication interface configured to communicate data indicating at least one treatment type and the plurality of appointments to the one or more medical devices used for providing treatment of the at least one treatment type.

13. A system according to claim 12, wherein
the plurality of instruction sets comprise device settings used for configuring the one or more medical devices to provide treatment for an individual appointment.

14. A system according to claim 10, wherein
the treatment type identifies first and second anatomical parts of a patient and the first and second prescribed treatments comprise first and second radiation doses to be applied to the first and second different body sites, respectively.

15. A system according to claim 10, wherein
the treatment type identifies an anatomical part of a patient and the first prescribed treatment comprises a radiation dose to be applied to the anatomical part and the second prescribed treatment comprises a non-radiation therapy.

16. A system according to claim 10, wherein the determined amount is a delay of at least one of (a) a first shift to a next subsequent appointment and (b) a second shift to a subsequent appointment following the next subsequent appointment.

* * * * *